US00PP37587P3

(12) United States Plant Patent
Olesen

(10) Patent No.: US PP37,587 P3
(45) Date of Patent: Aug. 18, 2026

(54) MINIATURE ROSE PLANT NAMED 'Poulpal107'

(50) Latin Name: *Rosa hybrida*
Varietal Denomination: Poulpal107

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/831,803

(22) Filed: Sep. 15, 2025

(65) Prior Publication Data

US 2026/0114339 P1 Apr. 23, 2026

(30) Foreign Application Priority Data

Sep. 19, 2024 (QZ) ..... PBR 20242189

(51) Int. Cl.
*A01H 6/74* (2018.01)
*A01H 5/02* (2018.01)

(52) U.S. Cl.
USPC ..... Plt./121
CPC ..... *A01H 6/749* (2018.05); *A01H 5/02* (2013.01)

(58) Field of Classification Search
USPC ..... Plt./101, 116, 121
See application file for complete search history.

(56) References Cited

U.S. PATENT DOCUMENTS

PP33,136 P2 * 6/2021 Olesen ..... Plt./238

* cited by examiner

*Primary Examiner* — Susan Mccormick Ewoldt

(57) ABSTRACT

A new garden rose plant of the Miniature class which has abundant, red-purple flowers and attractive foliage. This new and distinct variety has shown to be uniform and stable in the resulting generations from asexual propagation.

2 Drawing Sheets

Botanical designation: *Rosa hybrida.*
Variety denomination: 'Poulpal107'.

This application claims priority to Plant Breeder's Rights Application Number 2024/2189, which was filed at the Community Plant Variety Rights Office in the European Union on Sep. 19, 2024, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2017 and the resulting seeds were planted in a controlled environment in Odense, Denmark. The new variety, named 'Poulpal107', originated as a single seedling from the stated cross.

The new variety may be distinguished from its male pollen parent and female seed parent primarily by the following characteristics. The male pollen parent plant exhibits orange-pink blended flowers while the new variety has red-purple flowers. The female seed parent plant has light pink flowers while the new variety has a distinctly different red-purple flower colour.

The objective of the hybridization of this rose variety was to create a new and distinct variety with unique qualities, such as:

1. Uniform and abundant red-purple flowers;
2. Vigorous, but compact growth when propagated on its own roots;
3. Exceptional disease resistance; and
4. Suitability for production in small containers.

This combination of qualities is not present in previously available commercial cultivars of this type, known to the inventor, and distinguish 'Poulpal107' from all other varieties of which we are aware.

As part of the rose development program, Mogens N. Olesen germinated the seeds from the aforementioned hybridization during winter of 2017 and conducted evaluations on the resulting seedlings in a controlled environment in Odense, Denmark. 'Poulpal107' was selected in the spring of 2018 by the inventor as a single plant from the progeny of the aforementioned hybridization.

Asexual reproduction of 'Poulpal107' by rooted cuttings was first done by Mogens N. Olesen in the nursery in Odense, Denmark in July 2018. This initial and other subsequent asexual propagations conducted in controlled environments have demonstrated that the characteristics of 'Poulpal107' are true to type and are transmitted from one generation to the next.

DESCRIPTION OF THE DRAWING

The accompanying color illustrations show, as true as is reasonably possible to obtain in color photographs of this type, the typical characteristics of the buds, flowers, leaves, and stems, of 'Poulpal107'.

Specifically illustrated in FIG. 1 of the drawings are open flowers at various stages of development, and sepals and petals detached revealing reproductive flower parts.

Figure 1:
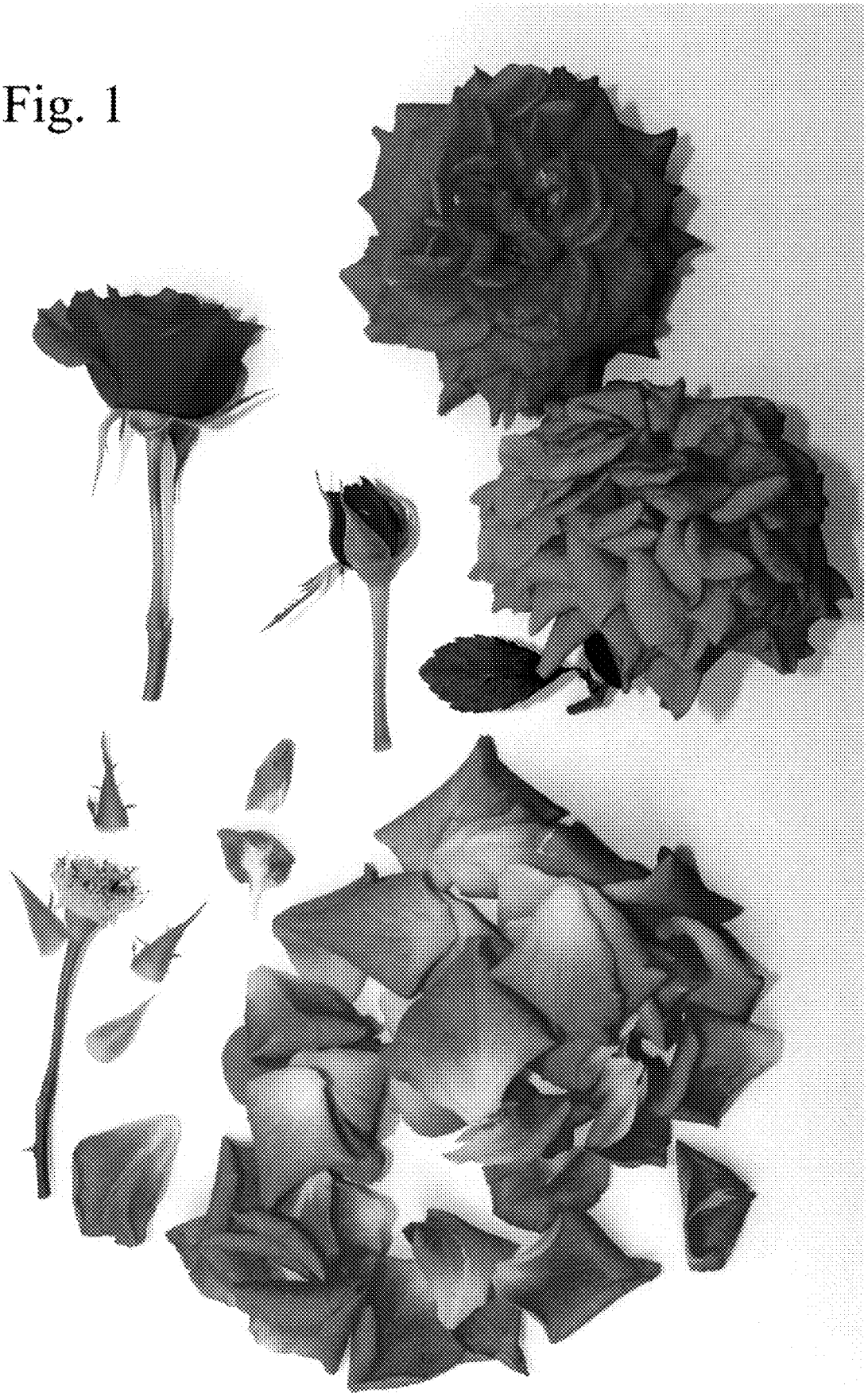
Figure 2:
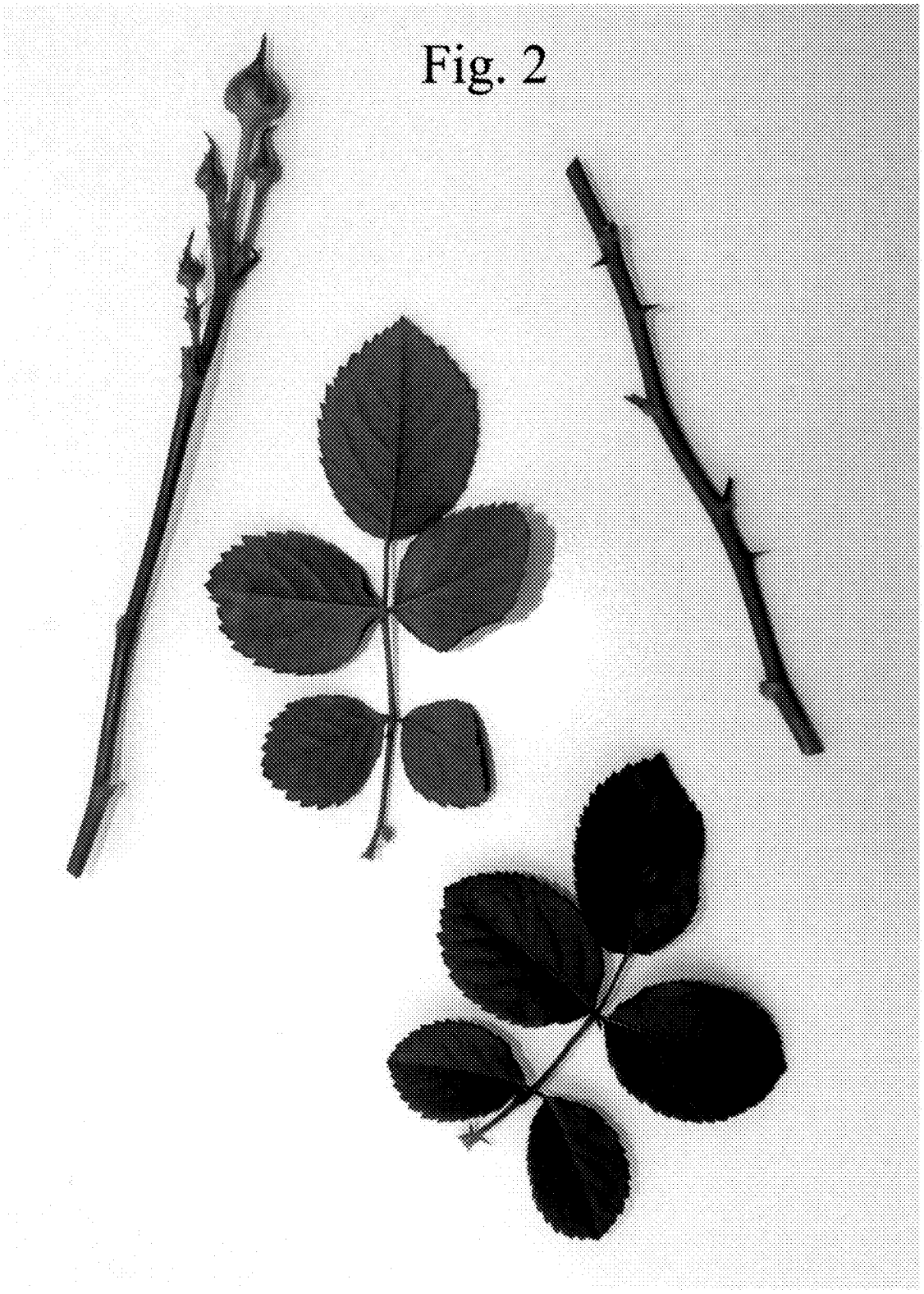

Specifically illustrated in FIG. 2 of the drawings are bare stems exhibiting prickles and flower buds, and mature leaves.

Plants shown are 3 months old.

DETAILED DESCRIPTION OF THE VARIETY

The following is a description of 'Poulpal107', as observed in its growth in a glasshouse nursery in Odense Denmark. Observed plants are 3 months of age, and were grown on their own roots in 30 cm pots. Color references are made using The Royal Horticultural Society (London, England) Colour Chart, 2001, except where common terms of color are used.

For a comparison, several physical characteristics of the rose variety 'Poulpah102', U.S. Plant Pat. No. 33,136, are compared to the claimed plant. While 'Poulpal107' has 45 flower petals, 'Poulpah102' has 85 to 90 flower petals. The claimed plant has a flower diameter of 70 mm while 'Poulpah102' has a flower diameter of 80 mm. Open flowers of 'Poulpal107' are generally are Red-Purple Group N57A becoming Red-Purple Group N57D as flowers mature. The comparison variety, 'Poulpah102', has a general tonality of Red-Purple Group N57C.

Flower and Flower Bud

Blooming habit: Continuous.

Flower bud:

- *Size.*—Upon opening, 25 mm in length from base of receptacle to end of bud. Bud diameter is 17 mm.
- *Bud form.*—Urceolate.
- *Bud color.*—As sepals divide petals are Red Group 53A and 53B.
- *Sepal inner surface.*—Color: Yellow-Green Group 146D. Surface: Lightly pubescent.
- *Sepal outer surface.*—Color: Yellow-Green Group 144A with intonations of Greyed-Red Group 180A. Texture: Smooth.
- *Sepal shape.*—Apex: Cirrhose. Base: Flat at union with receptacle.
- *Sepal margin.*—Margins have moderate or strong foliaceous appendages on three of the five sepals.
- *Sepal size.*—About 30 mm long, 10 mm wide.
- *Receptacle.*—Texture: Smooth. Size: 10 mm in height, 11 mm wide. Color: Yellow-Green Group 144A. Shape: Funnel.
- *Pedicel.*—Surface: Smooth. Length: 40 mm. Diameter: 3 mm on average. Color: Yellow-Green Group 144A with occasional intonations of Greyed-Red Group 180B. Strength: Strong.
- *Peduncle.*—Length: 2 to 4 cm. Diameter: About 3 mm. Color: Yellow-Green Group 145A. Texture: Smooth.

Flower bud development: Flower buds are borne in clusters of about 3 flower buds per stem.

Flower bloom:

- *Fragrance.*—Light floral scent.
- *Duration.*—The blooms have a duration on the plant of approximately 21 days. Petals fall cleanly away from plant after flowers have fully matured.
- *Size.*—Flower diameter is 70 mm when open. Flower depth is 50 mm.
- *Flower shape.*—Open, deep cup.
- *Shape of flower, side view.*—The upper portion is flat. The lower portion is flat concave becoming deep concave.

Petalage: Under normal conditions, flowers have about 45 petals.

General tonality of flower: Open flowers are Red-Purple Group N57A. After 7 days tonality changes to Red-Purple Group N57D.

Petal color:

- *Upon opening, outer petals.*—Upper surface: Red Group 52A with streaks of Red-Purple Group 62A. Lower surface: Red Group 52A.
- *Upon opening, inner petals.*—Upper surface: Red Group 52A with streaks of Red-Purple Group 62A. Lower surface: Red Group 53B.
- *Basal petal spots, upon opening.*—Upper surface: Yellow Group 8B. Lower surface: Yellow Group 8B.
- *After opening, outer petals.*—Upper surface: Red-Purple Group N57C with basal intonations of Red Group 56D. Lower surface: Red-Purple Group N57D with streaks of Red-Purple Group 65B.
- *After opening, inner petals.*—Upper surface: Red-Purple Group N57C with basal intonations of Red Group 56D. Lower surface: Red-Purple Group N57D with streaks of Red-Purple Group 65B.
- *Basal petal spots, after opening.*—Upper surface: Yellow Group 8B. Lower surface: Yellow Group 8B.

Petals:

- *Petal reflex.*—Moderate to strong.
- *Margin.*—Entire and uniform. Moderate undulations.
- *Shape.*—Broad and elliptic. Apex shape: Rounded. Base shape: Acute.
- *Size.*—46 mm (1) by 43 mm (w).
- *Texture.*—Smooth.
- *Thickness.*—Average.

Petaloids:

- *Size.*—29 mm (1) by 20 mm (w).
- *Quantity.*—About 10.
- *Shape.*—Elliptical with an acute base and rounded apices.
- *Color.*—Above, Red-Purple Group N57C. Underneath Red-Purple Group N57D. Occasional streaking of Red-Purple Group 65B.

Reproductive flower parts:

- *Pollen.*—None observed.
- *Anthers.*—Size: 2 mm in length. Color: Greyed-Orange Group 165C. Quantity: 40 on average.
- *Filaments.*—Color: Green-White Group 157A. Length: 10 mm.
- *Pistils.*—Length: 10 mm. Quantity: 40 on average.
- *Stigmas.*—Color: Yellow-White Group 158B.
- *Styles.*—Color: Yellow-White Group 158A with intonations of Red-Purple Group 61D.
- *Location of stigmas.*—Slightly inferior in location relative to the length of the filaments and the height of the anthers.
- *Hips.*—None Observed.

Plant

Plant growth: Upright. On average, plants are 40 cm in height, and 35 cm wide.

Stems:

- *Color of juvenile growth.*—Yellow-Green Group 144A.
- *Color of mature growth.*—Yellow-Green Group 146A.

*Length*.—Canes are about 25 cm from the base of the plant to the flowering portion.

*Diameter*.—About 4 mm.

*Internodes*.—On mature canes about 25-35 mm between nodes.

*Surface texture*.—Young wood: Smooth. Older wood: Smooth.

Long prickles:

*Incidence*.—4 prickles per 10 cm of stem.

*Size*.—Average length of prickles on mature stems is 6 mm.

*Shape*.—Upper portion is linear. Lower portion is Linear.

*Color*.—Juvenile prickles: Greyed-Red Group 180C. Mature prickles: Greyed-Red Group 180C and Greyed-Yellow Group 160C at the apex.

Plant foliage:

*Compound leaf*.—125 mm (1) x 95 (w).

*Quantity*.—3 leaves per 10 cm of stem on average.

*Leaf bearing angle to the stem*.—45 degrees.

*Color of juvenile foliage*.—Upper side: Yellow-Green Group 146A with intonations of Greyed-Purple Group 183B. Lower side: Yellow-Green Group 146B.

*Color of mature foliage*.—Upper side: Yellow-Green Group 147A. Lower side: Yellow-Green Group 147B.

Plant leaves and leaflets:

*Stipules*.—Size: 10 mm long, 3 mm wide. Quantity: 2 per compound leaf. Shape: Linear, slightly broad based with outward extending apices. Margins: Finely serrated. Color: Yellow-Green Group 144A.

*Petiole*.—Length: About 12 mm. Diameter: 2 mm. Upper surface color: Yellow-Green Group 144A. Lower surface color: Yellow-Green Group 144A.

*Rachis*.—Length: About 65 mm. Upper surface color: Yellow-Green Group 144A. Lower surface color: Yellow-Green Group 144A.

*Leaflet*.—Quantity: Normally 5 leaflets. Margins: Serrated.

*Size*.—Terminal leaflets are about 70 mm long, 45 mm wide.

*Shape*.—Generally elliptical. Base: Rounded. Apex: Mucronate.

*Texture*.—Smooth.

*Thickness*.—Average.

*Arrangement*.—Odd pinnate.

*Venation*.—Reticulate.

*Glossiness*.—Very glossy.

Disease resistance: Above average resistance to powdery mildew *Sphaerotheca pannosa* var. *rosae,* downy mildew *Peronospora sparsa,* rust *Phragmidium* spp., black spot *Diplocarpon rosae,* and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpal107' substantially as described and illustrated herein.

* * * * *